United States Patent
Tu et al.

(10) Patent No.: US 11,288,811 B2
(45) Date of Patent: Mar. 29, 2022

(54) VASCULAR PRESSURE DIFFERENCE CORRECTION METHOD, DEVICE AND APPARATUS

(71) Applicant: PULSE MEDICAL IMAGING TECHNOLOGY (SHANGHAI) CO. LTD., Shanghai (CN)

(72) Inventors: Shengxian Tu, Shanghai (CN); Wei Yu, Shanghai (CN); Jiayue Huang, Shanghai (CN); Yundai Chen, Shanghai (CN); Fuhua Yan, Shanghai (CN)

(*) Notice: Subject to any disclaimer, the term of this patent is extended or adjusted under 35 U.S.C. 154(b) by 0 days.

(21) Appl. No.: 17/266,253

(22) PCT Filed: Sep. 3, 2018

(86) PCT No.: PCT/CN2018/103783
§ 371 (c)(1),
(2) Date: Feb. 5, 2021

(87) PCT Pub. No.: WO2020/006853
PCT Pub. Date: Jan. 9, 2020

(65) Prior Publication Data
US 2021/0312636 A1    Oct. 7, 2021

(30) Foreign Application Priority Data
Jul. 2, 2018  (CN) .......................... 201810705804.X (51) Int. Cl.
*G06K 9/00*   (2006.01)
*G06T 7/149*  (2017.01)
(Continued)

(52) U.S. Cl.
CPC ............ *G06T 7/149* (2017.01); *G06T 11/203* (2013.01); *G06T 19/20* (2013.01);
(Continued)

(58) Field of Classification Search
CPC ................. G06T 7/0012; G06T 19/00; G06T 2207/10132; G06T 2210/41; G06T 7/11;
(Continued)

(56) References Cited

U.S. PATENT DOCUMENTS

| 2008/0009829 A1* | 1/2008 | Ta .......................... A61F 2/915 604/509 |
| 2011/0096996 A1* | 4/2011 | Mohamed ............... G06T 19/20 382/203 |

(Continued)

FOREIGN PATENT DOCUMENTS

| CN | 105072980 A | 11/2015 |
| CN | 106650029 A | 5/2017 |
| CN | 108022650 A | 5/2018 |

OTHER PUBLICATIONS

PCT International Search Report from Corresponding PCT/CN2018/103783 dated Mar. 27, 2019 (Chinese and English).
(Continued)

*Primary Examiner* — Guillermo M Rivera-Martinez
(74) *Attorney, Agent, or Firm* — Abelman, Frayne & Schwab; Stefan Knirr (57) ABSTRACT

A method, apparatus and device for correcting a vascular pressure difference are disclosed. An intracavity imaging technology is used to acquire images in a main branch blood vessel. A plurality of blood vessel cross sections are obtained using the images, and an area of a cutting plane of a side branch blood vessel is directly calculated by using the blood vessel cross sections. The blood vessel difference is then corrected by using the cutting area.

10 Claims, 6 Drawing Sheets

(51) Int. Cl.
*G06T 11/20* (2006.01)
*G06T 19/20* (2011.01)

(52) U.S. Cl.
CPC ............... *G06T 2207/10101* (2013.01); *G06T 2207/30101* (2013.01); *G06T 2207/30172* (2013.01); *G06T 2219/008* (2013.01)

(58) Field of Classification Search
CPC . G06T 2207/30101; G06T 2207/10101; G06T 2219/008; G06K 9/46
See application file for complete search history.

(56) References Cited

U.S. PATENT DOCUMENTS

| | | | | |
|---|---|---|---|---|
| 2012/0083696 | A1* | 4/2012 | Kitamura | G06T 7/33 600/443 |
| 2012/0130243 | A1* | 5/2012 | Balocco | A61B 8/12 600/443 |
| 2014/0379269 | A1 | 12/2014 | Schmitt | |
| 2015/0238121 | A1* | 8/2015 | Tu | A61B 5/0084 600/425 |
| 2015/0268039 | A1* | 9/2015 | Tu | A61B 6/481 702/19 |
| 2015/0356734 | A1* | 12/2015 | Ooga | A61B 6/5217 382/131 |
| 2016/0374710 | A1* | 12/2016 | Sinelnikov | A61B 8/481 600/439 |
| 2017/0103520 | A1* | 4/2017 | Gopinath | A61B 5/489 |
| 2017/0301084 | A1* | 10/2017 | Gopinath | G06T 5/002 |
| 2018/0116723 | A1* | 5/2018 | Hettrick | A61B 6/032 |

OTHER PUBLICATIONS

Notification to Grant Patent Right for Invention from Cn 201810705804.X dated Jun. 5, 2019 (Chinese and English).
First Office Action from CN 201810705804.x dated May 8, 2019 (Chinese and English).
First search from Cn 20181075804.X dated Apr. 26, 2019 (English).
International Preliminary Report on Patentability Chapter I from PCT/CN2018/103783 dated Mar. 27, 2019 (Chinese and English).

* cited by examiner

VASCULAR PRESSURE DIFFERENCE CORRECTION METHOD, DEVICE AND APPARATUS

CROSS REFERENCE TO RELATED APPLICATION

This application claims benefit under 35 U.S.C. § 371 to international application No. PCT/CN2018/103783 filed on Sep. 3, 2018, which claims priority to Chinese application No. 201810705804.X filed Jul. 2, 2018, the contents of which are incorporated by reference in their entireties.

TECHNICAL FIELD

The present invention belongs to the field of medical technologies, and in particular to a method, an apparatus and a device for correcting a blood vessel pressure difference.

BACKGROUND

The side-branch evaluation of a bifurcation lesion of a coronary artery has always been challenging in clinical practice and science. In a process in which this side-branch evaluation is performed by using an angiography technology, the angiography technology used involves optical coherence tomography (OCT), which is a high-resolution tomography technology and has a similar principle to intravascular ultrasound (IVUS). This technology uses near-infrared as a light source and uses interference of light waves to perform imaging. An optical signal obtained by beam scanning of a tissue is converted into an electrical signal, and the electrical signal is processed by a computer and then displayed as two-dimensional and three-dimensional images of gray or pseudo-color. Because the optical wavelength is shorter than the wavelength of sound waves, the optical coherence tomography has a higher resolution ranging from 10 um to 20 um. Compared with intravascular ultrasound, the optical coherence tomography can provide faster and clearer images, and more accurately display a specific shape of a blood vessel wall (whether the interior is blocked, a blocked area, a size, etc.).

Related to the side-branch evaluation of a bifurcation lesion of a coronary artery, the inventor of the present application disclosed a method for determining at least one geometric parameter of a side branch of a main branch of a blood vessel in the patent document US20150238121A1 published in an earlier US patent application, and the method includes: receiving a plurality of cross-section data sets, the data sets representing geometries of cross sections of the main branch over a length of the main branch; receiving position data of a cutting plane of the main branch, the cutting plane at least partially intersecting the side branch and the cutting plane, and the cutting plane intersects the cross section at an angle; based on data in at least a part of the plurality of cross section data sets, constructing image data of a constructed cross section of the main branch in the cutting plane; receiving contour data defining a contour in the constructed cross section, the contour being provided in the side branch; and determining the geometric parameter by determining a geometric parameter of the contour. The main branch refers to a main branch blood vessel in the coronary artery, and the side branch is a side branch blood vessel connected to the main branch blood vessel.

After blood vessel geometric parameters including a blood vessel diameter or a cross sectional area are obtained, a blood vessel pressure difference can be calculated according to the blood vessel geometric parameters. The blood vessel pressure difference is a pressure difference between a proximal start point and a distal end point of a blood vessel segment of interest, and is a parameter that can effectively reflect a blood supply function of the blood vessel. Because FFR (fractional flow reserve) is approximately equal to a ratio of a distal coronary pressure $P_d$ to a proximal coronary pressure $P_a$, FFR can be calculated from the blood vessel pressure difference between $P_d$ and $P_a$ and $P_a$ obtained through measurement.

The patent document CN108022650A discloses a method for calculating a blood vessel pressure difference based on parameters of a main branch blood vessel and a side branch blood vessel. This method involves obtaining of geometric parameters of the side branch blood vessel and calculation of an ideal vessel lumen geometric model, but there is still a problem of how to correct a value of the blood vessel pressure difference in this method.

SUMMARY

An objective of the present invention is to provide a method, an apparatus, and a device for correcting a blood vessel pressure difference, an intravascular image imaging technology is used to collect images in a main branch blood vessel, a plurality of blood vessel cross sections are obtained by using the images, an area of a cutting plane of a side branch blood vessel is directly calculated by using the blood vessel cross sections, and then the blood vessel pressure difference is corrected by using the cutting area.

One of the embodiments of the present invention provides a blood vessel pressure difference correction method. The blood vessel involved in the method includes a first blood vessel and a second blood vessel. The first blood vessel and the second blood vessel intersect and are connected. A distal demarcation point of the first blood vessel and the second blood vessel is a carina. The calculation method includes:

obtaining a plurality of blood vessel cross sections between a first end point and a second end point along a direction of a centerline of the first blood vessel by taking the proximal demarcation point of the first blood vessel and the second blood vessel as a second end point, and the carina as the first end point;

forming, by the blood vessel cross sections, contour lines on a first blood vessel wall and a second blood vessel wall;

enclosing, by the contour lines formed on the first blood vessel wall by the blood vessel cross sections, a plurality of first blood vessel convex surfaces;

enclosing, by the contour lines formed on the second blood vessel wall by the blood vessel cross sections, a plurality of second blood vessel convex surfaces;

intersecting, by the first blood convex surfaces and the second blood vessel convex surfaces, to form a plurality of intersection lines;

fitting the plurality of intersection lines into an intersection plane;

calculating an area of a cutting plane according to the intersection plane, where the cutting plane is a second blood vessel cross section perpendicular to a centerline of the second blood vessel cross the carina; and correcting the blood vessel pressure difference by using the area of the cutting plane.

The first blood vessel may be a main branch blood vessel of a coronary artery, and the second blood vessel may be a side branch blood vessel of the coronary artery.

One of the embodiments of the present invention provides a blood vessel pressure difference correction method, and the method includes:

receiving an intravascular tomographic image of a blood vessel segment of interest, the blood vessel segment including a proximal start point, at least one carina, and a distal end point;

obtaining a contour of a blood vessel lumen in the tomographic image by segmenting, and obtaining a geometric model of the blood vessel lumen by using three-dimensional reconstruction;

extracting parameters of a centerline of a side branch blood vessel according to the obtained geometric model of the blood vessel lumen;

making a cross section perpendicular to the centerline of the side branch blood vessel cross the carina;

calculating an area S of the side branch blood vessel on the cross section, that is, a cutting area of the side branch blood vessel; and correcting the blood vessel pressure difference according to the cutting area of the side branch blood vessel.

One of the embodiments of the present invention provides a blood vessel pressure difference correction apparatus. The apparatus is used to correct a calculation result of the blood vessel pressure difference. The apparatus includes an image imaging probe, a memory, and one or more processors coupled to the memory, and the processor is configured to execute instructions stored in the memory to perform imaging processing on image data obtained by the image imaging probe.

A blood vessel involved in the calculation of the blood vessel pressure difference includes a first blood vessel and a second blood vessel. The first blood vessel and the second blood vessel intersect and are connected. A distal demarcation point of the first blood vessel and the second blood vessel is a carina.

A plurality of blood vessel cross sections between a first end point and a second end point are obtained by using an image imaging probe, along a centerline of the first blood vessel, by taking the proximal demarcation point of the first blood vessel and the second blood vessel as the second end point, and taking the carina as the first end point. The processor performs the following operations:

the blood vessel cross sections form contour lines on a first blood vessel wall and a second blood vessel wall;

the contour lines formed on the first blood vessel wall by the blood vessel cross sections enclose a plurality of first blood convex surfaces;

the contour lines formed on the second blood vessel wall by the blood vessel cross sections enclose a plurality of second blood vessel convex surfaces;

the first blood convex surfaces and the second blood vessel convex surfaces intersect to form a plurality of intersection lines;

the plurality of intersection lines are fitted into an intersection plane;

an area of a cutting plane is calculated according to the intersection plane; and the blood vessel pressure difference is corrected by using the area of the cutting plane.

An image signal processing unit is connected to an image imaging probe by using a feeder, and the feeder is used to provide power for the image imaging probe and at the same time transmit a signal of the image imaging probe back to the image signal processing unit. An output end of the image signal processing unit is connected to the processor, so that the processor obtains image data in the first blood vessel and the second blood vessel. A display is connected to the processor, and is used to display an intravascular image obtained by the image imaging probe and data of the cutting plane obtained through calculation. An operation input unit is connected to the processor and is used to set operation parameters of the image imaging probe.

One of the embodiments of the present invention provides a blood vessel pressure difference correction device, and the device includes a blood vessel image data generation apparatus, a blood vessel pressure difference calculation apparatus, and a blood vessel pressure difference correction apparatus.

An output end of the blood vessel image data generation apparatus is respectively connected to an input end of the blood vessel pressure difference calculation apparatus and an input end of the blood vessel pressure difference correction apparatus, and the other input end of the blood vessel pressure difference correction apparatus is connected to an output end of the blood vessel pressure difference calculation apparatus.

The blood vessel pressure difference calculation apparatus calculates a blood vessel pressure difference value after obtaining blood vessel image data from the blood vessel image data generation apparatus.

The blood vessel pressure difference correction apparatus calculates and obtains area data of a cutting plane of a side branch blood vessel from the blood vessel image received by the blood vessel image data generation apparatus, receives the blood vessel pressure difference value from the blood vessel pressure difference calculation apparatus, correct the obtained blood vessel pressure difference value data according to the area data of the cutting plane, and obtain the corrected blood vessel pressure difference value.

One of the beneficial effects of the embodiments of the present invention is as follows: and contour lines of a cross section of a main branch and contour lines of a convex surface of a side branch are extracted from sequence images directly obtained in the main branch blood vessel by using an OCT or IVUS image imaging probe, and sequences of intersection lines formed by intersecting the two kinds of contour lines are fitted into an intersection plane, and an area of a cutting plane of the side branch is calculated according to the intersection plane. In this way, the calculation method in the prior art is improved, an estimation error in the existing calculation method is eliminated by the correction, and calculation accuracy of the geometric parameters of the side branch is improved.

One of the beneficial effects of the embodiments of the present invention is as follows: A geometric model of a blood vessel lumen is reconstructed by establishing blood vessel segments by using the method for calculating geometric parameters of a side branch provided in the embodiments. According to the geometric model of the blood vessel lumen, parameters of a centerline of the side branch blood vessel are extracted, a cross section of the side branch blood vessel is made on the centerline, and an area of the cross section is calculated, that is, an cutting area of the side branch blood vessel. The blood vessel pressure difference of the blood vessel segment is corrected according to the cutting area, so that accuracy of calculating fractional flow reserve FFR is improved.

One of the beneficial effects of the embodiments of the present invention is as follows: A blood vessel geometric parameter detection device including an image imaging probe, a memory, an image signal processing unit, a display, a processor, and an operation input unit provides cardiologists with a tool for quickly detecting and calculating geometric parameters of a side branch.

BRIEF DESCRIPTION OF THE DRAWINGS

The above and other objects, features and advantages of the exemplary embodiments of the present invention become easier to be understood by reading the following detailed description with reference to the accompanying drawings. In the drawings, several embodiments of the present invention are shown in an exemplary and non-limiting manner.

100—main branch, 102—main branch blood vessel wall,
200—side branch, 202—side branch blood vessel wall,
300—main branch centerline, 301—first main convex surface, 302—third main convex surface, 303—$n^{th}$ main convex surface,
400—side branch centerline, 401—first side convex surface, 402—third side convex surface, 403—$n^{th}$ side convex surface,
500—carina,
600—intersection plane, 601—first intersection line, 602—third intersection line,
603—$n^{th}$ intersection line,
700—cutting plane,
800—OCT probe.

DETAILED DESCRIPTION OF EMBODIMENTS

Embodiment 1

Figure 1:
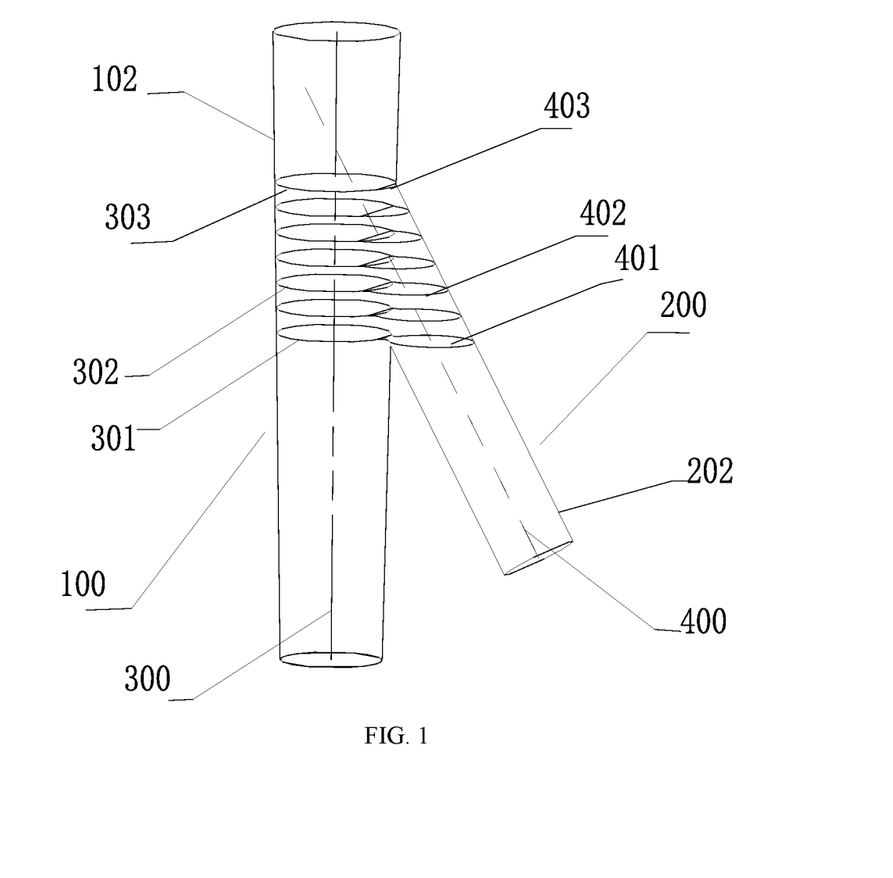
FIG. 1 is a schematic diagram of a blood vessel cross section of a main branch blood vessel and a side branch blood vessel according to an embodiment of the present invention.
Figure 4:
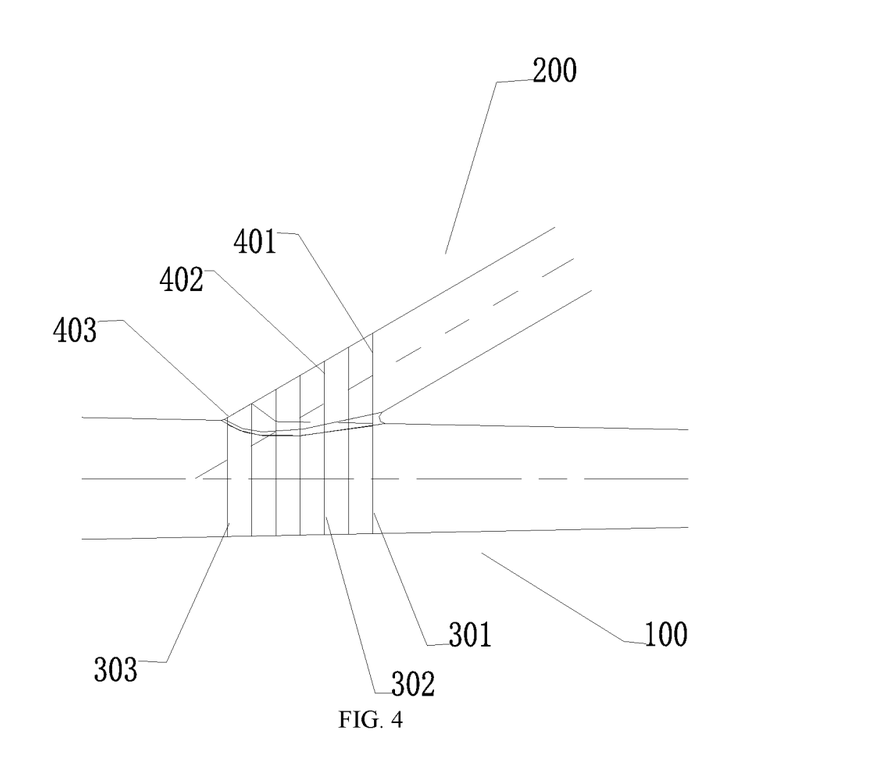
FIG. 4 is a lateral side view of FIG. 1.

As shown in FIG. 1 and FIG. 4, a first blood vessel is a main branch 100 and a second blood vessel is a side branch 200. The main branch 100 and the side branch 200 intersect and are connected at an angle, and a distal demarcation point of the main branch 100 and the side branch 200 is a carina 500. A blood vessel pressure difference correction method of the side branch 200 includes the following contents:

A plurality of blood vessel cross sections between a first end point and a second end point are obtained along a direction of a main branch centerline 300 by taking a proximal demarcation point of the main branch 100 and the side branch 200 as the second end point, and taking the carina 500 as the first end point.

The blood vessel cross sections form contour lines on the main branch blood vessel wall 102 and the side branch blood vessel wall 202.

The contour lines formed by the blood vessel cross sections on the main branch blood vessel wall 102 enclose a plurality of main convex surfaces, such as a first main convex surface 301, a third main convex surface 302, and a $n^{th}$ main convex surface 303 in FIG. 1.

The contour lines formed by the blood vessel cross sections on the side branch blood vessel wall 202 enclose a plurality of side convex surfaces, such as a first side convex surface 401, a third side convex surface 402, and a $n^{th}$ side convex surface 403 in FIG. 1.

Figure 2:
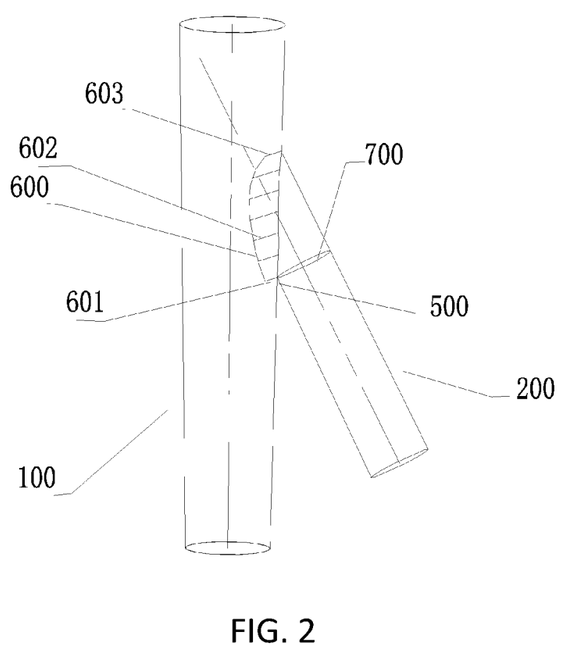
FIG. 2 is a schematic diagram of a plurality of intersection lines according to an embodiment of the present invention.

The main cross section and the side convex surface intersect to form a plurality of intersection lines, such as a first intersection line 601, a third intersection line 602, and a $n^{th}$ intersection line 603 in FIG. 2.

The plurality of intersection lines are fitted into an intersection plane, such as an intersection plane 600 as shown in FIG. 2.

Figure 3:
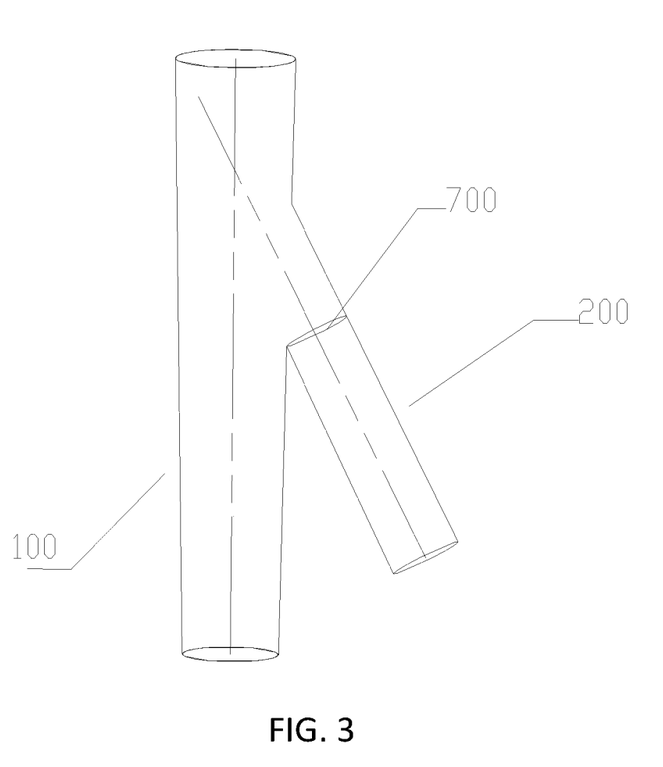
FIG. 3 is a schematic diagram of a cutting plane according to an embodiment of the present invention.

An area of a cutting plane 700 is calculated according to the intersection plane. The cutting plane 700 is shown in FIG. 2 and FIG. 3. The cutting plane 700 is a side branch cross section perpendicular to the side branch centerline 400 cross the carina 500. The area of the cutting plane 700=(an area of the intersection plane 600)*(the sine of the included angle between the main branch blood vessel centerline 300 and the side branch blood vessel centerline 400). The area of the cutting plane 700 is used to correct the blood vessel pressure difference.

Figure 6:
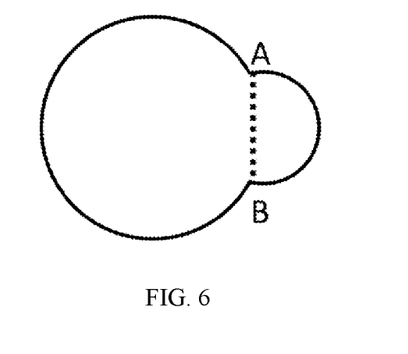
FIG. 6 is a schematic diagram of intersection lines formed by main convex surfaces and side convex surfaces of blood vessel cross sections according to an embodiment of the present invention.

According to one or more embodiments, as shown in FIG. 1, FIG. 4 and FIG. 6, in the blood vessel pressure difference correction and calculation, calculating the area of the cutting plane further includes:

identifying two points: point A and point B having the largest curvature changes on the contour line of the blood vessel cross section;

taking a straight line segment connecting point A and point B as a boundary line between the first blood vessel and the second blood vessel;

fitting the boundary lines formed by the plurality of blood vessel cross sections into a circular opening of the second blood vessel on the first blood vessel;

calculating an area $S_0$ of the circular opening;

obtaining the included angle θ between the centerline of the first blood vessel and the centerline of the second blood vessel, and obtaining the area of the cutting plane of the second blood vessel as:

$$S = S_0 \times \sin\theta \quad (1)$$

A value of the included angle θ can range from 0 to 180 degrees.

According to one or more embodiments, as shown in FIG. 4, distances between the blood vessel cross sections are equal.

Figure 5:
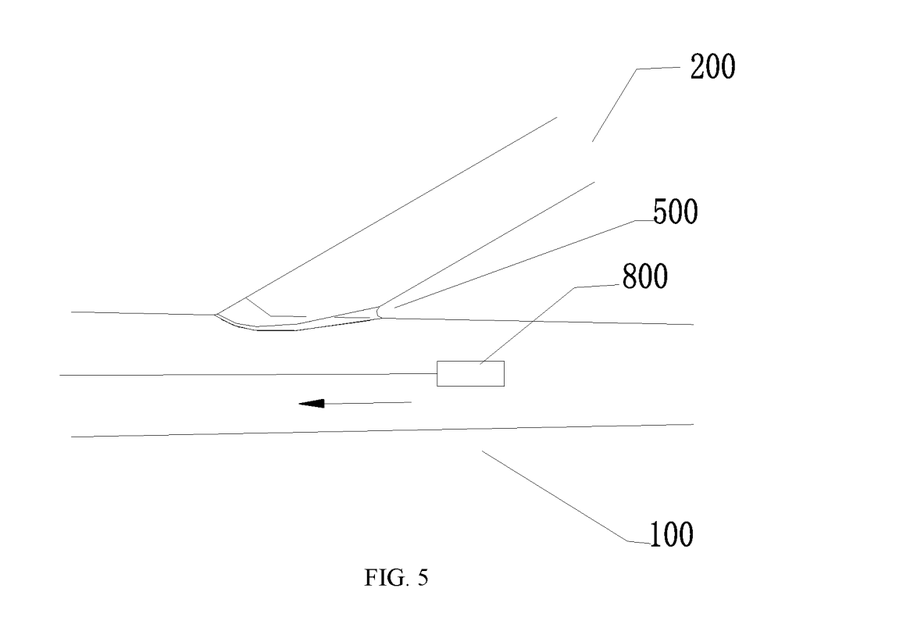
FIG. 5 is a schematic diagram of an intravascular image obtained by an OCT probe according to an embodiment of the present invention.

According to one or more embodiments, as shown in FIG. 5, the blood vessel cross section is obtained by performing scanning by an OCT probe 800 in the main branch along a direction of the main branch centerline 300. The OCT probe 800 passes through an intersection and connection region of the main branch and the side branch at a constant speed. The OCT probe 800 moves from the first end point to the second end point. An operation method is as follows: First, the OCT probe 800 is moved to a distal end of the main branch, then is withdrew at a constant speed, and passes through the region where the main branch and the side branch intersect, so that a plurality of images of blood vessel cross sections are obtained. In fact, the lumen diameter of the main branch blood vessel is not uniform. The OCT probe here can also be an IVUS probe.

Embodiment 2

According to one or more embodiments, a blood vessel pressure difference correction method is provided, and the method includes the following steps:

receive an intravascular tomographic image of a blood vessel segment of interest, the blood vessel segment including a proximal start point, at least one carina, and a distal end point;

obtain a contour of a blood vessel lumen in the tomographic image through segmenting, and obtain a geometric model of the blood vessel lumen through three-dimensional reconstruction;

extract parameters of a centerline of a side branch blood vessel according to the obtained geometric model of the blood vessel lumen;

make a cross section perpendicular to the centerline of the side branch blood vessel cross the carina;

calculate an area S of the side branch blood vessel on the cross section, that is, a cutting area of the side branch blood vessel; and correct the blood vessel pressure difference according to the cutting area of the side branch blood vessel.

The blood vessel segment includes the main branch blood vessel and the side branch blood vessel. The geometric parameters include a lumen area of the main branch blood vessel and a lumen area of the side branch blood vessel. The lumen area of the side branch blood vessel is also called an area of a cutting plane of the side branch blood vessel, and the cutting plane is the cross section of the side branch blood vessel perpendicular to the centerline of the side branch blood vessel cross the carina.

According to one or more embodiments, the blood vessel segment has a plurality of side branch blood vessels, and the main branch blood vessel is divided into a plurality of blood vessel segments according to the carinas of the side branch blood vessels. Assuming that the geometric model parameters of the blood vessel segment are embodied by the radius or diameter of the blood vessel cross section, parameters of the geometric model of the blood vessel lumen of the blood vessel segment can be calculated step by step with reference to a Murry formula, a Finet formula, a HK formula or an energy conservation model.

Figure 7:
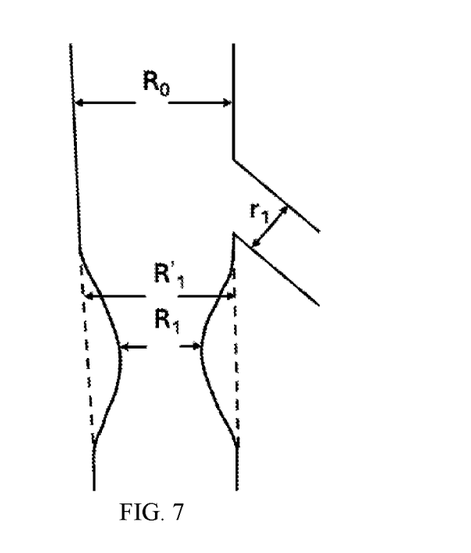
FIG. 7 is a schematic diagram of a lumen model of a multi-branched blood vessel according to an embodiment of the present invention.

As shown in FIG. 7, when there is a bifurcation in a blood vessel, a blood vessel segment between the bifurcation and a proximal start point of the blood vessel is normal, and there is stenosis in a blood vessel segment between the bifurcation and a distal end point of the blood vessel, geometric parameters of a lumen model of the blood vessel can be calculated with reference to the following methods. There is one side branch blood vessel in the blood vessel segment, and the main branch blood vessel is divided into two blood vessel segments according to the carina of the side branch blood vessel. $R_0$ represents a lumen radius of a proximal end of the blood vessel, and $R_0'$ represents an ideal lumen radius of the proximal end of the blood vessel (when the lumen of the proximal end of the blood vessel is normal, $R_0=R_0'$, and $S_0$ represents the lumen area of the proximal end of the blood vessel); $R_1$ represents a lumen radius of a distal end of the blood vessel, and $R_1'$ represents an ideal lumen radius of the distal end of the blood vessel (when the lumen of the distal end of the blood vessel is normal, $R_1=R_1'$, and S1 represents a lumen area of the distal end of the blood vessel); $C_1$ represents an area of a cutting plane of the bifurcation of the proximal end of the blood vessel, $r_1$ represents a radius of the cutting plane of the bifurcation of the proximal end of the blood vessel.

When the area $C_1$ of the cutting plane of the proximal bifurcation and the normal lumen area $S_0$ of the proximal end of the blood vessel are obtained, where $$r_1 = \sqrt{\frac{C_1}{\pi}}, \text{ and } R_0 = \sqrt{\frac{S_0}{\pi}},$$

an ideal lumen radius, diameter or area of the stenosis segment at the distal end of the blood vessel can be obtained by using a Murray formula of a bifurcation and shunt theorem. A calculation formula is as follows:

$$R_1'^3 = R_0^3 - r_1^3 \qquad (2).$$

Similarly, when there is a bifurcation in a blood vessel, there is stenosis in a blood vessel segment between the bifurcation and a proximal start point of the blood vessel, and a blood vessel segment between the bifurcation and a distal end point of the blood vessel is normal, geometric parameters of a lumen model of the blood vessel can be calculated with reference to the above similar method. When the area $C_1$ of the cutting plane of the proximal bifurcation and the normal lumen area $S_1$ of the distal end of the blood vessel are obtained, where $$r_1 = \sqrt{\frac{C_1}{\pi}}, \text{ and } R_1 = \sqrt{\frac{S_1}{\pi}},$$

an ideal lumen radius, diameter or area of the stenosis segment of the proximal end of the blood vessel can be obtained by using by a Murray formula of a bifurcation and shunt theorem. A calculation formula is as follows:

$$R_0'^3 = R_1^3 + r_1^3 \qquad (3).$$

Further, formulas such as Finet and HK of the bifurcation and shunt theorem or an energy conservation model can be used to calculate parameters such as the ideal lumen radius, diameter or area of the stenosis segment of the blood vessel. If the calculation method obtained by the Murray formula of the bifurcation and shunt theorem is taken as method (1), then:

Method (2): When the area $C_1$ of the cutting plane of the proximal bifurcation and the area $S_1$ of the normal lumen of the distal end of the blood vessel, where $$r_1 = \sqrt{\frac{C_1}{\pi}}, \text{ and } R_1 = \sqrt{\frac{S_1}{\pi}},$$

the ideal lumen radius, diameter or area of the stenotic segment of the distal end of the vessel can be obtained by using the Finet formula in the bifurcation and shunt theorem. The calculation formula is as follows:

$$R_1' = 1.475 R_0 - r_1 \qquad (4)$$

When there is a bifurcation in the blood vessel, there is stenosis in a blood vessel segment between the bifurcation and a proximal start point of the blood vessel, and a blood vessel segment between the bifurcation and a distal end point of the blood vessel is normal, a process of calculating geometric parameters of the blood vessel lumen model includes:

When the area $C_1$ of the cutting plane of the proximal bifurcation and the normal lumen area $S_1$ of the distal end of the blood vessel are obtained, where $$r_1 = \sqrt{\frac{C_1}{\pi}}, \text{ and } R_1 = \sqrt{\frac{S_1}{\pi}},$$

the ideal lumen radius, diameter or area of the stenosis segment of the proximal end of the blood vessel can be obtained by using the bifurcation and shunt theorem. A calculation formula is as follows:

$$R_0' = 0.678(R_1 + r_1) \tag{5}.$$

Method (3): When the area $C_1$ of the cutting plane of the proximal bifurcation and the normal lumen area $S_1$ of the distal end of the blood vessel are obtained, where $$r_1 = \sqrt{\frac{C_1}{\pi}}, \text{ and } R_1 = \sqrt{\frac{S_1}{\pi}},$$

the ideal lumen radius, diameter or area of the stenosis segment of the distal end of the blood vessel can be obtained by using the HK formula in the bifurcation and shunt theorem. A calculation formula is as follows:

$$R_1'^{\frac{7}{3}} = R_0^{\frac{7}{3}} - r_1^{\frac{7}{3}} \tag{6}$$

When there is a bifurcation in the blood vessel, there is stenosis in a blood vessel segment between the bifurcation and a proximal start point of the blood vessel, and a blood vessel segment between the bifurcation and a distal end point of the blood vessel is normal, a process of calculating geometric parameters of the blood vessel lumen model includes:

When the area $C_1$ of the cutting plane of the proximal bifurcation and the normal lumen area $S_1$ of the distal end of the blood vessel are obtained, where $$r_1 = \sqrt{\frac{C_1}{\pi}}, \text{ and } R_1 = \sqrt{\frac{S_1}{\pi}},$$

the ideal lumen radius, diameter or area of the stenosis segment of the proximal end of the blood vessel can be obtained by using the bifurcation and shunt theorem. A calculation formula is as follows:

$$R_0'^{\frac{7}{3}} = R_1^{\frac{7}{3}} + r_1^{\frac{7}{3}} \tag{7}.$$

Method (4): When the area $C_1$ of the cutting plane of the proximal bifurcation and the normal lumen area $S_1$ of the distal end of the blood vessel are obtained, where $$r_1 = \sqrt{\frac{C_1}{\pi}}, \text{ and } R_1 = \sqrt{\frac{S_1}{\pi}},$$

the ideal lumen radius, diameter or area of the stenosis segment at the distal end of the blood vessel are obtained by using the energy conservation model. A calculation formula is as follows:

$$R_1'^2 = R_0^2 - r_1^2 \tag{8}$$

When there is a bifurcation in the blood vessel, there is stenosis in a blood vessel segment between the bifurcation and a proximal start point of the blood vessel, and a blood vessel segment between the bifurcation and a distal end point of the blood vessel is normal, a process of calculating geometric parameters of the blood vessel lumen model includes:

When the area $C_1$ of the cutting plane of the proximal bifurcation and the normal lumen area $S_1$ of the distal end of the blood vessel are obtained, where $$r_1 = \sqrt{\frac{C_1}{\pi}}, \text{ and } R_1 = \sqrt{\frac{S_1}{\pi}},$$

the ideal lumen radius, diameter or area of the stenosis segment of the proximal end of the blood vessel are obtained by using the energy conservation model. A calculation formula is as follows:

$$R_0'^2 = R_1^2 + r_1^2 \tag{9}.$$

In the above formulas (2)~(9), definitions of the parameters involved are as follows:

$R_0$ represents the lumen radius of the proximal end of the blood vessel;

$R_0'$ represents the ideal lumen radius of the proximal end of the blood vessel (when the lumen of the proximal end of the blood vessel is normal, $R_0 = R_0'$, and $S_0$ represents the lumen area of the proximal end of the blood vessel);

$R_1$ represents the lumen radius of the distal end of the blood vessel;

$R_1'$ represents the ideal lumen radius of the distal end of the blood vessel (when the lumen of the distal end of the blood vessel is normal, $R_1 = R_1'$, and $S_1$ represents the lumen area of the distal end of the blood vessel);

$C_1$ represents the area of the cutting plane of the proximal end of the vessel; and $r_1$ represents the radius of the cutting plane of the bifurcation of the proximal end of the blood vessel.

Further, when the blood vessel has a plurality of branches and there is stenosis in some blood vessel segments, the ideal lumen radius, diameter and area of the stenosis segment of the blood vessel can be calculated step by step by using the bifurcation and shunt theorem with reference to the above method.

Further, the geometric parameters of the lumen geometric model of the blood vessel segment in the plurality of blood vessel segments are one or a combination of the following parameters: the cross sectional area of the blood vessel lumen, the diameter of the blood vessel lumen, and the radius of the blood vessel lumen. Considering the stenosis of the blood vessel segment, the geometric parameters include a first geometric parameter that represents a cross sectional area or diameter of a distal end of the blood vessel segment; a second geometric parameter representing a cross sectional area or diameter of the first bifurcation in a range between the stenosis of the blood vessel segment and the distal end point; a third geometric parameter representing a cross sectional area or diameter of the second bifurcation in a range between the stenosis of the blood vessel segment and the distal end point; . . . ; a $(1+n)^{th}$ geometric parameter representing a cross sectional area or diameter of the $n^{th}$ bifurcation in a range between the stenosis of the blood vessel segment and the distal end point.

Embodiment 3

Figure 8:
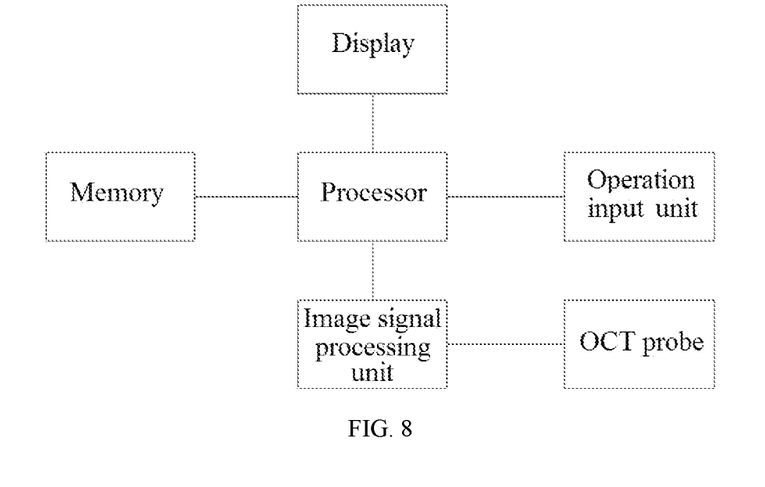
FIG. 8 is a schematic diagram of a composition of a blood vessel pressure difference correction apparatus according to an embodiment of the present invention.

FIG. 8 is a schematic diagram of a composition of a blood vessel pressure difference correction apparatus according to an embodiment of the present invention.

A blood vessel pressure difference correction apparatus is provided. The apparatus includes an OCT probe, a memory, an image signal processing unit, a display, and an operation input unit, and one or more processors coupled to the memory. The image signal processing unit is connected to the OCT probe 800 by using a feeder, and the feeder is used to provide power for a light source of the OCT probe 800, and at the same time transmit a signal of the OCT probe 800 back to the image signal processing unit. An output end of the image signal processing unit is connected to the processor, so that the processor obtains image data in a main branch and a side branch. The display is connected to the processor, and is used to display an intravascular image obtained by the OCT probe 800 and data of a cutting plane 700 obtained through calculation. The operation input unit is connected to the processor and is used to set operating parameters of the OCT probe 800.

The processor is configured to execute instructions stored in the memory, and the processor performs the following operations:

A plurality of blood vessel cross sections between a first end point and a second end point are obtained by using the OCT probe 800, along a main branch centerline 300, by taking a proximal demarcation point between a main branch 100 and a side branch 200 is the second end point, and taking a carina 500 as the first end point. The blood vessel cross sections form contour lines on a main blood vessel wall 102 and a side branch blood vessel wall 202.

The contour lines formed on the main branch blood vessel wall 102 by the blood vessel cross sections enclose a plurality of main convex surfaces. The contour lines formed on the side branch blood vessel wall 202 by the blood vessel cross sections enclose a plurality of side convex surfaces.

The main convex surfaces and the side convex surfaces intersect to form a plurality of intersection lines. The plurality of intersection lines are fitted into an intersection plane 600. An area of the cutting plane 700 is calculated according to the intersection plane 600. The area of the cutting plane 700=(an area of the intersection plane 600)*(the sine of an included angle between the centerline 300 of the main branch blood vessel and the centerline 400 of the side branch blood vessel). Then, the blood vessel pressure difference is corrected by using the area of the cutting plane 700. The OCT probe here can also be an IVUS probe.

Embodiment 4

Figure 9:
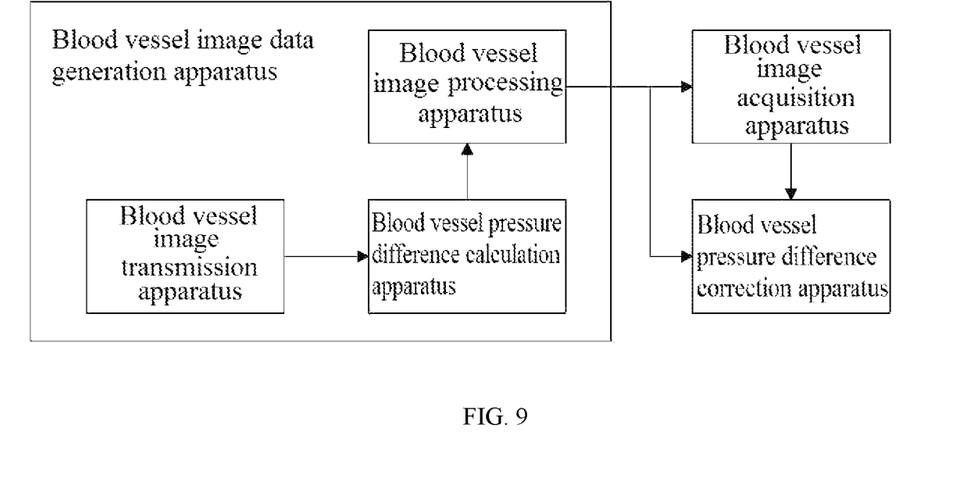
FIG. 9 is a schematic diagram of a composition of a blood vessel pressure difference correction device according to an embodiment of the present invention.

As shown in FIG. 9, a blood vessel pressure difference correction device is provided. The device includes a blood vessel image data generation apparatus, a blood vessel pressure difference calculation apparatus, and a blood vessel pressure difference correction apparatus.

An output end of the blood vessel image data generation apparatus is respectively connected to an input end of the blood vessel pressure difference calculation apparatus and an input end of the blood vessel pressure difference correction apparatus, and the other input end of the blood vessel pressure difference correction apparatus is connected to an output end of the blood vessel pressure difference calculation apparatus.

The blood vessel pressure difference calculation apparatus calculates a blood vessel pressure difference value after obtaining blood vessel image data from the blood vessel image data generation apparatus.

The blood vessel pressure difference correction apparatus receives, from the blood vessel image data generation apparatus, the area data that is of the cutting plane of the side branch blood vessel in the blood vessel image and that is obtained through calculation according to the method described in Embodiment 1, and receives the blood vessel pressure difference value from the blood vessel pressure difference calculation apparatus, corrects the obtained blood vessel pressure difference value according to the area data of the cutting plane, and obtains the corrected blood vessel pressure difference value.

Preferably, the blood vessel image data generation apparatus includes a blood vessel image acquisition apparatus, a blood vessel image transmission apparatus, and a blood vessel image processing apparatus. An output end of the blood vessel image acquisition apparatus is sequentially connected to the blood vessel image transmission apparatus and the blood vessel image processing apparatus. An output end of the blood vessel image processing apparatus is respectively connected to an input end of the blood vessel pressure difference calculation apparatus and an input end of the blood vessel pressure difference correction apparatus.

Preferably, the blood vessel image data generation apparatus adopts a blood vessel lumen tomography method or an intravascular ultrasound angiography method to obtain blood vessel lumen geometric data, including using an OCT or IVUS technology. The blood vessel pressure difference correction apparatus can correct the blood vessel pressure difference value by using the calculation method of the geometric parameters of the blood vessel lumen (for example, the area of the cutting plane of the side branch blood vessel) involved in Embodiment 1 according to the data obtained from the blood vessel image processing apparatus. Alternatively, the blood vessel pressure difference correction apparatus described in Embodiment 3 can be used to independently obtain the geometric parameters of the blood vessel lumen (for example, the area of the cutting plane of the side branch blood vessel), and correct the blood vessel pressure difference value according to the geometric parameters.

A person of ordinary skill in the art can understand that all or part of the processes in the above embodiment methods can be implemented by instructing relevant hardware by using a computer program. The program can be stored in a computer readable storage medium. When the program is executed, the procedures of the above method embodiments may be included. The storage medium may be a magnetic disk, an optical disk, a read-only memory (Read-Only Memory, ROM), or a random access memory (Random Access Memory, RAM), etc.

It is worth noting that although the foregoing content has described the spirit and principle of the present invention with reference to several specific embodiments, the present invention is not limited to the disclosed specific embodiments, and the division of various aspects does not mean that the features in these aspects cannot be combined. This division is only for the convenience of presentation. The present invention is intended to cover various modifications and equivalent arrangements included within the spirit and scope of the appended claims.

The invention claimed is:

1. A blood vessel pressure difference correction method, wherein a blood vessel involved in the method comprises a first blood vessel and a second blood vessel, the first blood vessel and the second blood vessel intersect and are connected, and a distal demarcation point of the first blood vessel and the second blood vessel is a carina, and the method comprises:

obtaining a plurality of blood vessel cross sections between a first end point and a second end point along a direction of a centerline of the first blood vessel by taking a proximal demarcation point of the first blood vessel and the second blood vessel as the second end point, and taking the carina as the first end point;

forming, by the blood vessel cross sections, contour lines on a first blood vessel wall and a second blood vessel wall;

enclosing, by the contour lines formed on the first blood vessel wall by the blood vessel cross sections, a plurality of first blood vessel convex surfaces;

enclosing, by the contour lines formed on the second blood vessel wall by the blood vessel cross sections, a plurality of second blood vessel convex surfaces;

intersecting, by the first blood vessel convex surfaces and the second blood vessel convex surfaces, to form a plurality of intersection lines;

fitting the plurality of intersection lines into an intersection plane;

calculating an area of a cutting plane according to the intersection plane, wherein the cutting plane is a second blood vessel cross section perpendicular to a centerline of the second blood vessel cross the carina; and correcting a blood vessel pressure difference by using the area of the cutting plane, wherein the calculating an area of a cutting plane further comprises:

identifying two points: point A and point B having the largest curvature changes on the contour line of the blood vessel cross section;

taking a straight line segment connecting point A and point B as a boundary line between the first blood vessel and the second blood vessel;

fitting boundary lines formed by the plurality of blood vessel cross sections into a circular opening of the second blood vessel on the first blood vessel;

calculating an area $S_0$ of the circular opening;

obtaining an included angle $\theta$ between the centerline of the first blood vessel and the centerline of the second blood vessel, and obtaining the area of the cutting plane of the second blood vessel as:

$$S = S_0 \times \sin\theta \quad (1)$$

wherein preferably, a value range of the included angle $\theta$ is 0~180 degrees.

2. The blood vessel pressure difference correction method according to claim 1, wherein the first blood vessel is a main branch blood vessel of a coronary artery, and the second blood vessel is a side branch blood vessel of the coronary artery.

3. The blood vessel pressure difference correction method according to claim 1, wherein the blood vessel cross section is extracted from an intravascular imaging image, preferably, the intravascular imaging image is obtained by an image imaging probe by performing scanning in the first blood vessel along the direction of the centerline of the first blood vessel, and preferably, the image imaging probe is an optical coherence tomography (OCT) image sensor probe or an intravascular ultrasound (IVUS) image sensor probe.

4. The blood vessel pressure difference correction method according to claim 3, wherein when the image imaging probe moves through an intersection and connection region of the first blood vessel and the second blood vessel, images in the first blood vessel are obtained at equal distance intervals; and preferably, when the image imaging probe moves back from the first end point to the second end point, the plurality of blood vessel cross sections are obtained.

5. A blood vessel pressure difference correction method, wherein the method comprises:

receiving an intravascular tomographic image of a blood vessel segment of interest, the blood vessel segment comprising a proximal start point, at least one carina, and a distal end point;

obtaining a contour of a blood vessel lumen in the tomographic image by segmenting, and obtaining a geometric model of the blood vessel lumen by using three-dimensional reconstruction;

extracting parameters of a centerline of a side branch blood vessel according to the obtained geometric model of the blood vessel lumen;

making a cross section perpendicular to the centerline of the side branch blood vessel cross the carina;

calculating an area S of the side branch blood vessel on the cross section, that is a cutting area of the side branch blood vessel; and correcting a blood vessel pressure difference according to the cutting area of the side branch blood vessel, wherein there is at least one bifurcation in the blood vessel segment, and when a blood vessel segment between the bifurcation and a proximal start point of the blood vessel is normal, and there is stenosis in a blood vessel segment between the bifurcation and a distal end point of the blood vessel, or there is stenosis in a blood vessel segment between the bifurcation and a proximal start point of the blood vessel, and a blood vessel segment between the bifurcation and a distal end point of the blood vessel is normal, a process of calculating the geometric parameters of the blood vessel lumen model comprises one or more of the following methods:

definitions of the parameters involved comprise:

$R_0$ represents a lumen radius of a proximal end of the blood vessel;

$R_0'$ represents an ideal lumen radius of the proximal end of the blood vessel, and when the lumen of the proximal end of the blood vessel is normal, $R_0 = R_0'$, and $S_0$ represents a lumen area of the proximal end of the blood vessel;

$R_1$ represents a lumen radius of a distal end of the blood vessel;

$R_1'$ represents an ideal lumen radius of the distal end of the blood vessel, and when the lumen of the distal end of the blood vessel is normal, $R_1 = R_1'$, and $S_1$ represents a lumen area of the distal end of the blood vessel lumen;

$C_1$ represents an area of a cutting plane of the bifurcation of the proximal end of the blood vessel;

$r_1$ represents a radius of the cutting plane of the bifurcation of the proximal end of the blood vessel;

method (1): obtaining the area $C_1$ of the cutting plane of the bifurcation of the proximal end, and the area $S_0$ of the normal lumen of the proximal end of the blood vessel, wherein $r_1=\sqrt{C_1/\pi}$, and $R_0=\sqrt{S_0/\pi}$, obtaining the ideal lumen radius, diameter or area of the stenosis segment of the distal end of the blood vessel by using a Murray formula in a bifurcation and shunt theorem, and a calculation formula is as follows:

$$R_1'^3 = R_0^3 - r_1^3 \quad (2)$$

when there is a bifurcation in the blood vessel, there is stenosis in a blood vessel segment between the bifurcation and a proximal start point of the blood vessel, and a blood vessel segment between the bifurcation and a distal end point of the blood vessel is normal, the process of calculating the geometric parameters of the blood vessel lumen model comprises:

obtaining the area $C_1$ of the cutting plane of the bifurcation of the proximal end and the area $S_1$ of the normal lumen of the distal end of the blood vessel, wherein $r_1=\sqrt{C_1/\pi}$, and $R_1=\sqrt{S_1/\pi}$, obtaining the ideal lumen radius, diameter or area of the stenosis segment of the proximal end of the blood vessel according to the bifurcation and shunt theorem, wherein a calculation formula is as follows:

$$R_0'^3 = R_1^3 + r_1^3 \quad (3)$$

method (2): obtaining the area $C_1$ of the cutting plane of the bifurcation of the proximal end, and the area $S_0$ of the normal lumen of the proximal end of the blood vessel, wherein $r_1=\sqrt{C_1/\pi}$, and $R_0=\sqrt{S_0/\pi}$, obtaining the ideal lumen radius, diameter or area of the stenotic segment of the distal end of the blood vessel by using a Finet formula in the bifurcation and shunt theorem, wherein a calculation formula is as follows:

$$R_1' = 1.475 R_0 - r_1 \quad (4)$$

when there is a bifurcation in the blood vessel, there is stenosis in a blood vessel segment between the bifurcation and a proximal start point of the blood vessel, and a blood vessel segment between the bifurcation and a distal end point of the blood vessel is normal, the process of calculating the geometric parameters of the blood vessel lumen model comprises:

obtaining the area $C_1$ of the cutting plane of the bifurcation of the proximal end and the area $S_1$ of the normal lumen of the distal end of the blood vessel, wherein $r_1=\sqrt{C_1/\pi}$, $R_1=\sqrt{S_1/\pi}$, obtaining the ideal lumen radius, diameter or area of the stenosis segment of the proximal end of the blood vessel according to the bifurcation and shunt theorem, wherein a calculation formula is as follows:

$$R_0' = 0.678(R_1 + r_1) \quad (5);$$

method (3): obtaining the area $C_1$ of the cutting plane of the bifurcation of the proximal end, and the area $S_0$ of the normal lumen of the proximal end of the blood vessel, wherein $r_1=\sqrt{C_1/\pi}$, and $R_0=\sqrt{S_0/\pi}$, obtaining the ideal lumen radius, diameter or area of the stenotic segment of the distal end of the blood vessel by using a HK formula in the bifurcation and shunt theorem, wherein a calculation formula is as follows:

$$R_1'^{7/3} = R_0^{7/3} - r_1^{7/3} \quad (6)$$

when there is a bifurcation in the blood vessel, there is stenosis in a blood vessel segment between the bifurcation and a proximal start point of the blood vessel, and a blood vessel segment between the bifurcation and a distal end point of the blood vessel is normal, the process of calculating the geometric parameters of the blood vessel lumen model comprises:

obtaining the area $C_1$ of the cutting plane of the bifurcation of the proximal end and the area $S_1$ of the normal lumen of the distal end of the blood vessel, wherein $r_1=\sqrt{C_1/\pi}$, $R_1=\sqrt{S_1/\pi}$, obtaining the ideal lumen radius, diameter or area of the stenosis segment of the proximal end of the blood vessel according to the bifurcation and shunt theorem, wherein a calculation formula is as follows:

$$R_0'^{7/3} = R_1^{7/3} - r_1^{7/3} \quad (7)$$

method (4): obtaining the area $C_1$ of the cutting plane of the bifurcation of the proximal end, and the area $S_0$ of the normal lumen of the proximal end of the blood vessel, wherein $r_1=\sqrt{C_1/\pi}$, and $R_0\sqrt{S_0/\pi}$, obtaining the ideal lumen radius, diameter or area of the stenotic segment of the distal end of the blood vessel by using an energy conservation model, wherein a calculation formula is as follows:

$$R_1'^2 = R_0^2 - r_1^2 \quad (8)$$

when there is a bifurcation in the blood vessel, there is stenosis in a blood vessel segment between the bifurcation and a proximal start point of the blood vessel, and a blood vessel segment between the bifurcation and a distal end point of the blood vessel is normal, the process of calculating the geometric parameters of the blood vessel lumen model comprises:

obtaining the area $C_1$ of the cutting plane of the bifurcation of the proximal end and the area $S_1$ of the normal lumen of the distal end of the blood vessel, wherein $r_1=\sqrt{C_1/\pi}$, $R_1=\sqrt{S_1/\pi}$, obtaining the ideal lumen radius, diameter or area of the stenosis segment of the proximal end of the blood vessel according to the bifurcation and shunt theorem, wherein a calculation formula is as follows:

$$R_0'^2 = R_1^2 + r_1^2 \quad (9).$$

6. The blood vessel pressure difference correction method according to claim 5, wherein the geometric parameters of the lumen geometric model of the blood vessel segment are one or a combination of the following parameters: the cross sectional area of the blood vessel lumen, the diameter of the blood vessel lumen, the radius of the blood vessel lumen, preferably, considering the stenosis of the blood vessel segment, the geometric parameters comprise a first geometric parameter representing the cross sectional area or diameter of the distal end of the blood vessel segment;

a second geometric parameter representing the cross sectional area or diameter of the first bifurcation in a range between the stenosis of the blood vessel segment and the distal end point;

a third geometric parameter representing the cross sectional area or diameter of the second bifurcation in a range between the stenosis of the blood vessel segment and the distal end point; and a $(1+n)^{th}$ geometric parameter representing the cross sectional area or diameter of the $n^{th}$ bifurcation in a range between the stenosis of the blood vessel segment and the distal end point.

7. A blood vessel pressure difference correction apparatus, configured to correct a calculation result of a blood vessel pressure difference, wherein the apparatus comprises an image imaging probe, a memory, and one or more processors coupled to the memory, and the processor is configured to execute instructions stored in the memory to perform imaging processing on the image data obtained by the image imaging probe, a blood vessel involved in calculation of the blood vessel pressure difference comprises a first blood vessel and a second blood vessel, the first blood vessel and the second blood vessel intersect and are connected, and a distal demarcation point of the first blood vessel and the second blood vessel is a carina, and a plurality of blood vessel cross sections between a first end point and a second end point are obtained by using the image imaging probe, along a centerline of the first blood vessel, by taking a proximal demarcation point of the first blood vessel and the second blood vessel as the second end point, and taking the carina as the first end point;

the processor performs the following operations:

the blood vessel cross sections form contour lines on a first blood vessel wall and a second blood vessel wall;

the contour lines formed on the first blood vessel wall by the blood vessel cross sections enclose a plurality of first blood convex surfaces;

the contour lines formed on the second blood vessel wall by the blood vessel cross sections enclose a plurality of second blood vessel convex surfaces;

the first blood convex surfaces and the second blood vessel convex surfaces intersect to form a plurality of intersection lines;

the intersection lines are fitted in to an intersection plane;

an area of a cutting plane is calculated according to the intersection plane; and the blood vessel pressure difference is corrected by using the area of the cutting plane, wherein the calculating an area of a cutting plane further comprises:

identifying two points: point A and point B having the largest curvature changes on the contour line of the blood vessel cross section;

taking a straight line segment connecting point A and point B as a boundary line between the first blood vessel and the second blood vessel;

fitting boundary lines formed by the plurality of blood vessel cross sections into a circular opening of the second blood vessel on the first blood vessel;

calculating an area $S_0$ of the circular opening;

obtaining an included angle θ between the centerline of the first blood vessel and the centerline of the second blood vessel, and obtaining the area of the cutting plane of the second blood vessel as:

$$S = S_0 \times \sin \theta \quad (1)$$

wherein preferably, a value range of the included angle θ is 0~180 degrees.

8. The blood vessel pressure difference correction apparatus according to claim 7, wherein the correction apparatus further comprises an image signal processing unit, a display and an operation input unit, the image signal processing unit is connected to the image imaging probe by using a feeder, and the feeder is used to provide power for the image imaging probe and at the same time transmit a signal of the image imaging probe back to the image signal processing unit, an output end of the image signal processing unit is connected to the processor, so that the processor obtains image data in the first blood vessel and the second blood vessel, the display is connected to the processor, and is used to display an intravascular image obtained by the image imaging probe and data of the cutting plane obtained through calculation, and the operation input unit is connected to the processor, and is used to set operation parameters of the image imaging probe.

9. A blood vessel pressure difference correction device, comprising a blood vessel image data generation apparatus, a blood vessel pressure difference calculation apparatus, and a blood vessel pressure difference correction apparatus, an output end of the blood vessel image data generation apparatus is respectively connected to an input end of the blood vessel pressure difference calculation apparatus and an input end of the blood vessel pressure difference correction apparatus, and the other input end of the blood vessel pressure difference correction apparatus is connected to an output end of the blood vessel pressure difference calculation apparatus, the blood vessel pressure difference calculation apparatus calculates a blood vessel pressure difference value after obtaining blood vessel image data from the blood vessel image data generation apparatus, and the blood vessel pressure difference correction apparatus obtains area data of the cutting plane of a side branch blood vessel from the blood vessel image received by the blood vessel image data generation apparatus, receives the blood vessel pressure difference value from the blood vessel pressure difference calculation apparatus, correct the obtained blood vessel difference value according to the area date data of the cutting plane, and obtain the corrected blood vessel difference value, wherein the calculating an area of a cutting plane further comprises:

identifying two points: point A and point B having the largest curvature changes on the contour line of the blood vessel cross section;

taking a straight line segment connecting point A and point B as a boundary line between the first blood vessel and the second blood vessel;

fitting boundary lines formed by the plurality of blood vessel cross sections into a circular opening of the second blood vessel on the first blood vessel;

calculating an area $S_0$ of the circular opening;

obtaining an included angle θ between the centerline of the first blood vessel and the centerline of the second blood vessel, and obtaining the area of the cutting plane of the second blood vessel as:

$$S = S_0 \times \sin \theta \quad (1)$$

wherein preferably, a value range of the included angle θ is 0~180 degrees.

10. The blood vessel pressure difference correction device according to claim 9, wherein the blood vessel image data generation apparatus comprises a blood vessel image acquisition apparatus, a blood vessel image transmission apparatus, and a blood vessel image processing apparatus, an output end of the blood vessel image acquisition apparatus is sequentially connected to the blood vessel image transmission apparatus and the blood vessel image processing apparatus, and an output end of the blood vessel image processing apparatus is respectively connected to an input end of the blood vessel pressure difference calculation apparatus and an input end of the blood vessel pressure difference correction apparatus; or, the blood vessel image data generation apparatus adopts a blood vessel lumen angiography method to obtain geometric data of a blood vessel lumen.

\* \* \* \* \*